US012788373B2

(12) United States Patent
Haugaard et al.

(10) Patent No.: US 12,788,373 B2
(45) Date of Patent: Nov. 10, 2026

(54) ULTRASOUND SYSTEM FOR AUTOMATICALLY DETERMINING FLOW REGIONS IN AN ULTRASOUND IMAGE AND DISPLAYING FLOW INFORMATION IN THE FLOW REGIONS

(71) Applicant: GE Precision Healthcare LLC, Waukesha, WI (US)

(72) Inventors: Per Haugaard, Skovlunde (DK); Svetoslav Nikolov, Søborg (DK); Mikkel Schou, Roskilde (DK)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/054,106

(22) Filed: Feb. 14, 2025

(65) Prior Publication Data

US 2026/0240527 A1 Aug. 20, 2026

(51) Int. Cl.
*A61B 8/00* (2006.01)
*A61B 8/06* (2006.01)

(52) U.S. Cl.
CPC .............. *A61B 8/5246* (2013.01); *A61B 8/06* (2013.01); *A61B 8/4494* (2013.01); *A61B 8/463* (2013.01); *A61B 8/488* (2013.01); *A61B 8/5223* (2013.01)

(58) Field of Classification Search
CPC ....... A61B 8/5246; A61B 8/06; A61B 8/4494; A61B 8/463; A61B 8/488; A61B 8/5223
See application file for complete search history.

(56) References Cited

U.S. PATENT DOCUMENTS

| | | | | |
|---|---|---|---|---|
| 6,093,149 | A | 7/2000 | Guracar et al. | |
| 6,450,959 | B1 | 9/2002 | Mo et al. | |
| 11,346,929 | B2 | 5/2022 | Vignon et al. | |
| 11,529,118 | B2 | 12/2022 | Lu | |
| 11,944,497 | B2 | 4/2024 | Du et al. | |
| 2015/0209012 | A1 | 7/2015 | Oh et al. | |
| 2019/0239753 | A1 * | 8/2019 | Wentz | G01J 3/2803 |
| 2021/0161510 | A1 * | 6/2021 | Sasaki | A61B 8/461 |
| 2024/0180523 | A1 * | 6/2024 | Bappoo | A61B 8/488 |
| 2024/0331285 | A1 * | 10/2024 | Bloms | G06T 7/0012 |
| 2025/0261562 | A1 * | 8/2025 | Firouzi | H10N 30/88 |

* cited by examiner

*Primary Examiner* — Sanjay Cattungal
(74) *Attorney, Agent, or Firm* — SPQ IP LLC

(57) ABSTRACT

An ultrasound system may acquire ultrasound data of a region of interest of a subject. The ultrasound system may generate an ultrasound image of the region of interest of the subject based on the ultrasound data. The ultrasound system may determine one or more flow regions in the ultrasound image. The ultrasound system may acquire the flow information corresponding to the one or more flow regions based on determining the one or more flow regions in the ultrasound image. The ultrasound system may display the ultrasound image and the flow information corresponding to the one or more flow regions in the ultrasound image.

20 Claims, 11 Drawing Sheets

ULTRASOUND SYSTEM FOR AUTOMATICALLY DETERMINING FLOW REGIONS IN AN ULTRASOUND IMAGE AND DISPLAYING FLOW INFORMATION IN THE FLOW REGIONS

TECHNICAL FIELD

The present disclosure relates to an ultrasound system for automatically determining flow regions in an ultrasound image and displaying flow information in the flow regions. More specifically, the present disclosure relates to an ultrasound system that acquires ultrasound data of a region of interest of a subject, generates an ultrasound image of the region of interest of the subject, determines one or more flow regions in the ultrasound image, acquires flow information corresponding to the one or more flow regions, and displays the ultrasound image and the flow information.

BACKGROUND

An ultrasound system may generate a B-mode ultrasound image which is a two-dimensional image of a region of interest of a subject and which displays various structures of the region of interest in gray-scale. For instance, the ultrasound system may transmit ultrasound signals towards the region of interest, receive echo signals that are reflected by, or back-scattered from the region of interest, and generate a B-mode ultrasound image based on the amplitude of the echo signals. In some cases, the ultrasound system may also acquire flow information of a particular region of the region of interest using a flow imaging technique. For example, the ultrasound system may use a power Doppler technique to determine the presence of flow in the particular region of the region of interest, and display a B-mode image that is overlaid with flow information that depicts the presence of flow in the particular region. As another example, the ultrasound system may use a color Doppler technique to determine the velocity and direction of flow in the particular region of the region of interest, and display a B-mode image that is overlaid with flow information that depicts the velocity and direction of flow in the particular region. As yet another example, the ultrasound system may use a vector flow imaging technique to determine the velocity and direction of flow at any point within the particular region of the region of interest, and display a B-mode image that is overlaid with flow information that depicts the velocity and direction of flow at any point within the particular region of the region of interest in the particular region. As yet another example, the ultrasound system may use a spectral Doppler technique to determine the velocity of flow along a particular line (e.g., a continuous-wave (CW) Doppler line or a pulsed-wave (PW) Doppler line) and/or within a particular gate (e.g., a PW Doppler gate) over time.

With the foregoing flow imaging techniques, the ultrasound system might require the user to select the location of the particular single region of the region of interest for acquiring the flow information. For example, the ultrasound system may display a single box that delineates a single specific region that is a limited subset of the B-mode ultrasound image and that identifies the position for which flow information is to be acquired. In this case, the user may interact with a user interface to position the single box to correspond to a particular region of the region of interest for which the flow information is to be acquired. As another example, the user may interact with a position and/or orientation of a CW Doppler line or a PW Doppler line and PW Doppler gate to set the particular region of the region of interest for which the flow information is to be acquired. In this way, the ultrasound system requires a manual user interaction to set the location of the single particular region for which flow information is to be acquired. These manual user interactions may be cumbersome for the user, might reduce the efficiency of imaging procedures, etc.

However, in some cases, the region of interest may include multiple regions that exhibit fluid flow. In these cases, the ultrasound system might not be capable of simultaneously, or substantially simultaneously, acquiring flow information of the multiple regions that exhibit fluid flow because the ultrasound system is limited to acquiring flow information for the particular single region delineated by the single box or delineated by the CW Doppler line or the PW Doppler line and PW Doppler gate. Moreover, the ultrasound system might not be capable of acquiring flow information for an entire field-of-view of the ultrasound image due to processing constraints, memory constraints, bandwidth constraints, latency constraints, etc. Accordingly, the displayed ultrasound image might not comprehensively display flow information for the entire field-of-view.

SUMMARY

This summary introduces concepts that are described in more detail in the detailed description. It should not be used to identify essential features of the claimed subject matter, nor to limit the scope of the claimed subject matter.

In an aspect, an ultrasound system may have transducer elements configured to acquire ultrasound data of a region of interest of a subject and acquire flow information of the region of interest of the subject; an acoustic matching layer configured to match an impedance differential between the transducer elements and the subject; a backing layer configured to attenuate the ultrasound signals transmitted by the transducer elements; a memory configured to store instructions; and one or more processors configured to execute the instructions to: acquire the ultrasound data of the region of interest of the subject; generate an ultrasound image of the region of interest of the subject based on the ultrasound data; determine one or more flow regions in the ultrasound image; acquire the flow information corresponding to the one or more flow regions based on determining the one or more flow regions in the ultrasound image; and display the ultrasound image and the flow information corresponding to the one or more flow regions in the ultrasound image.

In an aspect, the one or more processors may be configured to determine the one or more flow regions using an image processing technique.

In an aspect, the one or more processors may be configured to determine the one or more flow regions using an artificial intelligence model.

In an aspect, the one or more processors may be configured to determine the one or more flow regions using preoperative imaging data of the region of interest of the subject acquired by a preoperative imaging system.

In an aspect, the one or more processors may be configured to: display a prompt to a user of the ultrasound system that prompts the user to accept respective one or more locations of the one or more flow regions.

In an aspect, the one or more processors may be configured to automatically acquire the flow information corresponding to the one or more flow regions without receiving a user input that sets respective one or more locations of the one or more flow regions.

In an aspect, the one or more processors may be configured to refrain from acquiring other flow information corresponding to external regions that are external to the one or more flow regions.

In another aspect, a method may include acquiring ultrasound data of a region of interest of a subject; generating an ultrasound image of the region of interest of the subject based on the ultrasound data; determining one or more flow regions in the ultrasound image; acquiring flow information corresponding to the one or more flow regions based on determining the one or more flow regions in the ultrasound image; and displaying the ultrasound image and the flow information corresponding to the one or more flow regions in the ultrasound image.

In yet another aspect, a non-transitory computer-readable medium may store instructions that, when executed by one or more processors, cause the one or more processors to: acquire ultrasound data of a region of interest of a subject; generate an ultrasound image of the region of interest of the subject based on the ultrasound data; determine one or more flow regions in the ultrasound image; acquire the flow information corresponding to the one or more flow regions based on determining the one or more flow regions in the ultrasound image; and display the ultrasound image and the flow information corresponding to the one or more flow regions in the ultrasound image.

DETAILED DESCRIPTION

As addressed above, an ultrasound system might require a user to select a location of the particular single region of a region of interest for acquiring the flow information. For example, the ultrasound system may display a single box that delineates a single specific region that is a subset of the B-mode ultrasound image and that identifies the position for which flow information is to be acquired. In this way, the ultrasound system requires a manual user interaction to set the location of the single particular region for which flow information is to be acquired. In other cases, the ultrasound system might not be capable of simultaneously, or substantially simultaneously, acquiring flow information of the multiple regions that exhibit fluid flow. Moreover, the ultrasound system might not be capable of acquiring flow information for an entire field-of-view of the ultrasound image due to processing constraints, memory constraints, bandwidth constraints, latency constraints, etc.

Some embodiments herein provide an ultrasound system that acquires ultrasound data of a region of interest of a subject; generates an ultrasound image of the region of interest of the subject based on the ultrasound data; determines one or more flow regions in the ultrasound image; acquires flow information corresponding to the one or more flow regions based on determining the one or more flow regions in the ultrasound image; and displays the ultrasound image and the flow information corresponding to the one or more flow regions in the ultrasound image. In this way, the ultrasound system automatically determines the one or more flow regions in the ultrasound image and displays flow information in the one or more flow regions. Further, in this way, the ultrasound system reduces the need for a manual user input of setting a particular region of the ultrasound image for flow information acquisition, and increases the amount of flow information that is capable of being displayed in real-time on the ultrasound image.

Accordingly, some embodiments herein provide an improvement to the technical field of ultrasound imaging, provide an improvement to user interfaces of ultrasound systems, and provide an improvement to ultrasound systems by reducing the amount of user inputs for flow information acquisition and by improving the amount of flow information that is capable of being displayed in real-time on the ultrasound image.

Figure 1:
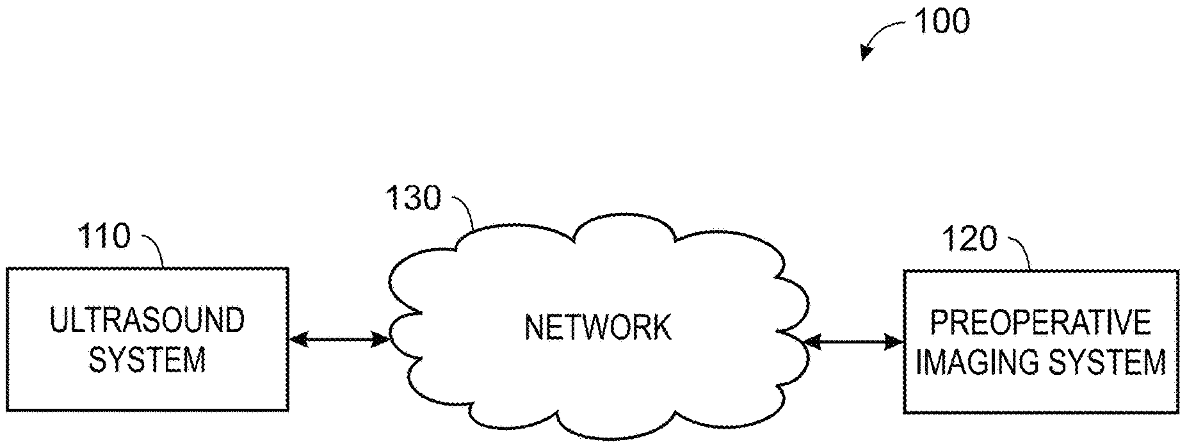
FIG. 1 is a diagram of an example system for automatically determining flow regions in an ultrasound image and displaying flow information in the flow regions.

FIG. 1 is a diagram of an example system 100 for automatically determining flow regions in an ultrasound image and displaying flow information in the flow regions. As shown in FIG. 1, the system 100 may include an ultrasound system 110, a preoperative imaging system 120, and a network 130.

The ultrasound system 110 may be configured to acquire ultrasound data of a region of interest of a subject, and acquire flow information of the region of interest of the subject. For example, the ultrasound system 110 may be a two-dimensional (2D) ultrasound system, a three-dimensional (3D) ultrasound system, a four-dimensional (4D) ultrasound system, a Doppler ultrasound system, or the like. The subject may be a person, an animal, a phantom, or the like. The region of interest may be any anatomical region of the subject. For example, the region of interest may be a heart, a brain, an organ, a blood vessel, or the like.

The preoperative imaging system 120 may be configured to acquire preoperative imaging data of the region of interest of the subject. For example, the preoperative imaging system 120 may be a computed tomography (CT) system, a magnetic resonance imaging (MRI) system, an ultrasound system, an X-ray system, a positron emission tomography (PET) device, or the like.

The network 130 may permit communication between the ultrasound system 110 and the preoperative imaging system 120. For example, the network 130 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

The number and arrangement of the system 100 are provided as an example. In practice, the system 100 may include additional systems, fewer systems, different systems, or differently arranged systems than those shown in FIG. 1. Additionally, or alternatively, a set of systems (e.g., one or more systems) of the system 100 may be integrated into a single system, and/or perform one or more functions described as being performed by another system, or set of systems, of the system 100.

Figure 2:
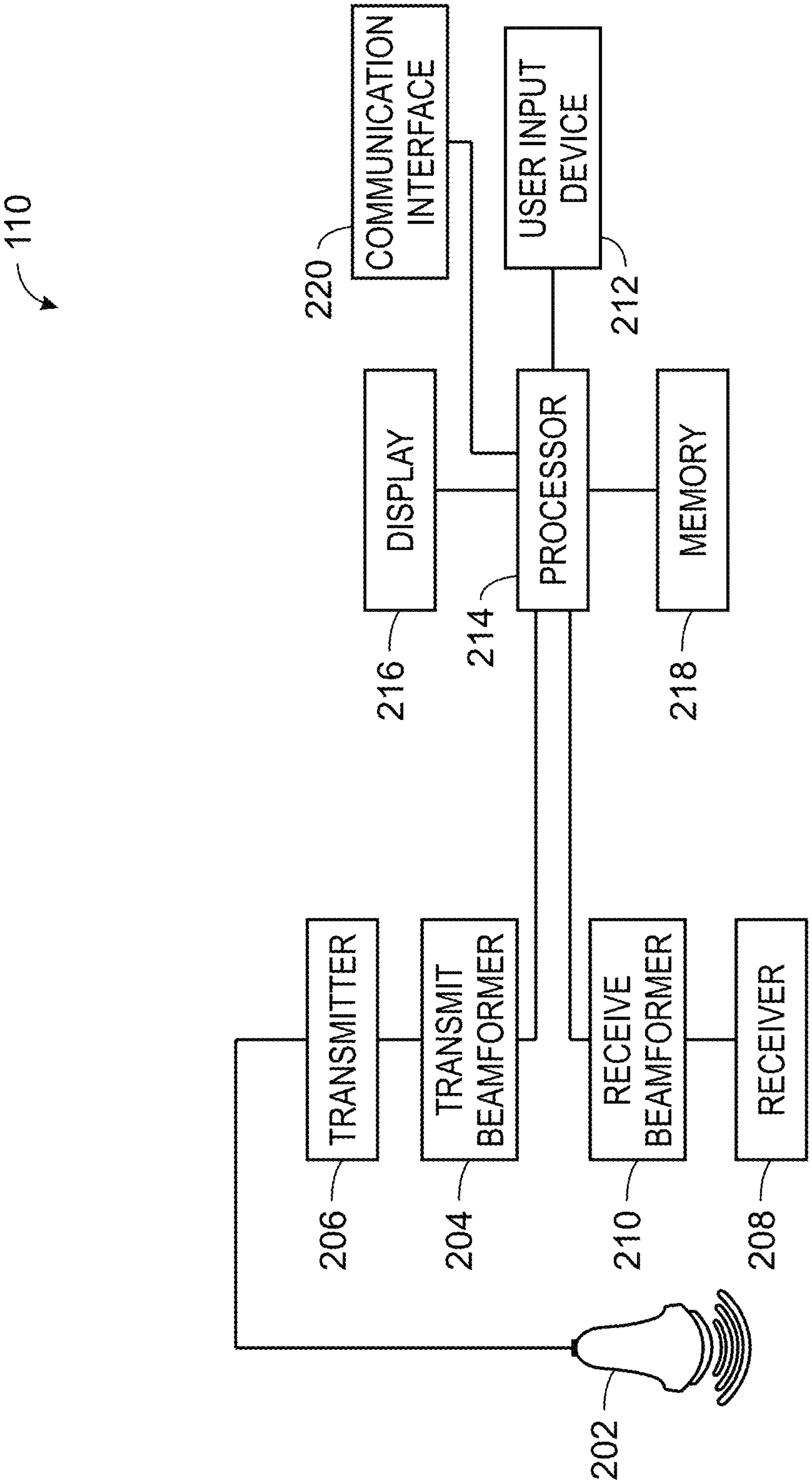
FIG. 2 is a diagram of an example ultrasound system of FIG. 1.

FIG. 2 is a diagram of an example ultrasound system of FIG. 1. As shown in FIG. 2, the ultrasound system 110 may include an ultrasound probe 202, a transmit beamformer 204, a transmitter 206, a receiver 208, a receive beamformer 210, a user input device 212, a processor 214, a display 216, a memory 218, and a communication interface 220. The foregoing components may be connected via wired or wireless connections.

The ultrasound probe 202 may be configured to acquire ultrasound data of a region of interest of a subject, and acquire flow information of the region of interest of the subject. For example, the ultrasound probe 202 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 202 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data.

The transmit beamformer 204 may be configured to apply delay times to electrical signals provided to the transducer elements of the ultrasound probe 202 to focus corresponding ultrasound signals at the region of interest. The transmitter 206 may be configured to transmit electrical signals to the transducer elements to drive the transducer elements to emit ultrasound signals towards the region of interest. The transducer elements may be configured to receive the electrical signals from the transmitter 206, convert the electrical signals into ultrasound signals, and emit the ultrasound signals towards the region of interest. The transducer elements may be configured to receive echo ultrasound signals that are back-scattered by the region of interest, convert the echo ultrasound signals into electrical signals, and provide the electrical signals to the receiver 208. The receiver 208 may be configured to receive electrical signals from the transducer elements, and provide the electrical signals to the receive beamformer 210. The receive beamformer 210 may apply delay times to the electrical signals received from the transducer elements.

The user input device 212 may be configured to receive a user input, and provide the user input to the processor 214. For example, the user input device 212 may be a user interface, a touch screen display, a keyboard, a keypad, a mouse, a button, a switch, a microphone, or the like. Additionally, or alternatively, the user input device 212 may be configured to sense information. For example, the user input device 212 may sense information from an electromagnetic positioning system, an inertial measurement system, an accelerometer, a gyroscope, an actuator, or the like.

The processor 214 may be configured to perform the operations as described herein. For example, the processor 214 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 214 may be implemented in hardware, firmware, or a combination of hardware and software. The processor 214 may include one or more processors 214 configured to perform the operations described herein. For example, a single processor 214 may be configured to perform all of the operations described herein. Alternatively, multiple processors 214, collectively, may be configured to perform all of the operations described herein, and each of the multiple processors 214 may be configured to perform a subset of the operations described herein. For example, a first processor 214 may perform a first subset of the operations described herein, a second processor 214 may be configured to perform a second subset of the operations described herein, etc.

The processor 214 may be configured to control the ultrasound probe 202 to acquire ultrasound data. The processor 214 may be configured to control which of the transducer elements are active, and control the shape of a beam emitted from the ultrasound probe 202. The processor 214 may generate ultrasound images for display, and may generate flow information for display. For example, the processor 214 may generate B-mode images, color Doppler images, M-mode images, color M-mode images, or the like. The ultrasound images may be 3D images, 2D images, single plane images, bi-plane images, three-plane images, multi-plane images, or the like. The flow information may be power Doppler imaging information, spectral Doppler information, color velocity imaging information, vector flow imaging information, The ultrasound images may correspond to various anatomical planes (e.g., sagittal, coronal, and transverse) of the region of interest.

The display 216 may be configured to display information. For example, the display 216 may be a monitor, an LED display, a cathode ray tube, a projector display, a touchscreen, tablet computer, mobile phone, virtual reality (VR) and/or augmented reality (AR) glasses, or the like. The display 216 may display ultrasound images based on the ultrasound data in real-time. For example, the display 216 may display the ultrasound images within one second, two seconds, five seconds, etc., of the ultrasound data being acquired by the ultrasound probe 202.

The memory 218 may be configured to store information and/or instructions for use by the processor 214. The memory 218 may be a non-transitory computer-readable medium. For example, the memory 218 may be a random access memory (RAM), a read only memory (ROM), and/or another type of dynamic or static storage device (e.g., a flash memory, a magnetic memory, and/or an optical memory) that stores information and/or instructions for use by the processor 214. The memory 218 may be configured to store instructions that, when executed by the processor 214, cause the processor 214 to perform the operations described herein.

The communication interface 220 may be configured to enable the processor 214 to communicate with other systems, such as via a wired connection, a wireless connection, or a combination of wired and wireless connections. For example, the communication interface 220 may include an Ethernet interface, an optical interface, a coaxial interface, an infrared interface, a radio frequency (RF) interface, a universal serial bus (USB) interface, a Wi-Fi interface, a cellular network interface, or the like.

The number and arrangement of the components of the ultrasound system 110 shown in FIG. 2 are provided as an example. In practice, the ultrasound system 110 may include additional components, fewer components, different components, or differently arranged components than those shown in FIG. 2. Additionally, or alternatively, a set of components (e.g., one or more components) of the ultrasound system 110 may perform one or more functions described as being performed by another set of components of the ultrasound system 110.

Figure 3:
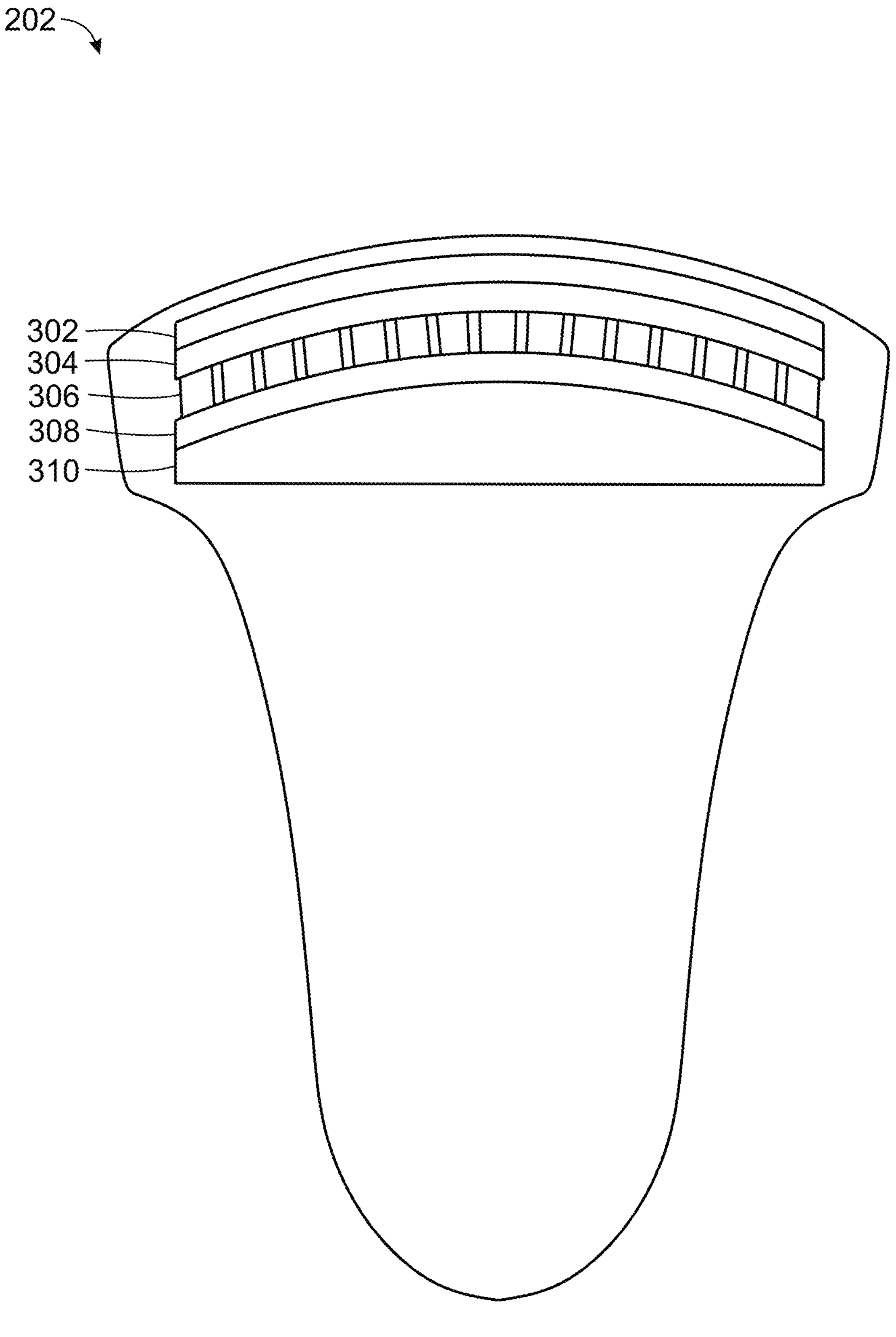
FIG. 3 is a diagram of example components of an ultrasound probe of FIG. 2.

FIG. 3 is a diagram of example components of an ultrasound probe of FIG. 2. As shown in FIG. 3, the ultrasound probe 202 may include a lens 302, an acoustic matching layer 304, transducer elements 306, an acoustic dematching layer 308, and a backing layer 310.

According to an embodiment, the lens 302 may be configured to direct an ultrasound signal towards the region of interest of the subject. For example, the lens 302 may be silicone, epoxy, rubber, or the like. According to an embodiment, the acoustic matching layer 304 may be configured to facilitate matching of an impedance differential that may exist between the relatively high impedance transducer elements 306 and the relatively low impedance subject. For example, the acoustic matching layer 304 may be graphite, plastic, resin, or the like. According to an embodiment, the transducer elements 306, respectively, may be configured to receive an element specific transmit signal, transform the element specific transmit signal to an ultrasound signal, and transmit the ultrasound signal towards a region of interest. Additionally, or alternatively, the transducer elements 306 may be configured to receive an echo signal reflected by or backscattered from the region of interest, transform the echo signal to an electrical signal, and transmit the electrical signal. For example, the transducer elements 306 may be piezoelectric materials, such as $Pb(Mg_{1/3}Nb_{2/3})O_3$—$PbTiO_3$ ("PMN-PT"), $Pb(In_{1/2}Nb_{1/2})O_3$—$Pb(Mg_{1/3}Nb_{2/3})O_3$—$PbTiO_3$ ("PIN-PMN-PT"), Pb(ZrTi) ("PZT"), or the like. According to an embodiment, the acoustic dematching layer 308 may be configured to decrease insertion losses and enhance a frequency bandwidth of the transducer elements 306. For example, the acoustic dematching layer 308 may be tungsten carbide, silicon carbide, or the like. According to an embodiment, the backing layer 310 may be configured to attenuate ultrasound signals directed from the transducer elements 306 in a direction opposite to the subject, and attenuate ultrasound signals deflected by a housing of the ultrasound probe 202. For example, the backing layer 310 may be an epoxy, a metal, or the like.

The number and arrangement of the components of the ultrasound probe 202 shown in FIG. 3 are provided as an example. In practice, the ultrasound probe 202 may include additional components, fewer components, different components, or differently arranged components than those shown in FIG. 3. Additionally, or alternatively, a set of components (e.g., one or more components) of the ultrasound probe 202 may perform one or more functions described as being performed by another set of components of the ultrasound probe 202.

Figure 4:
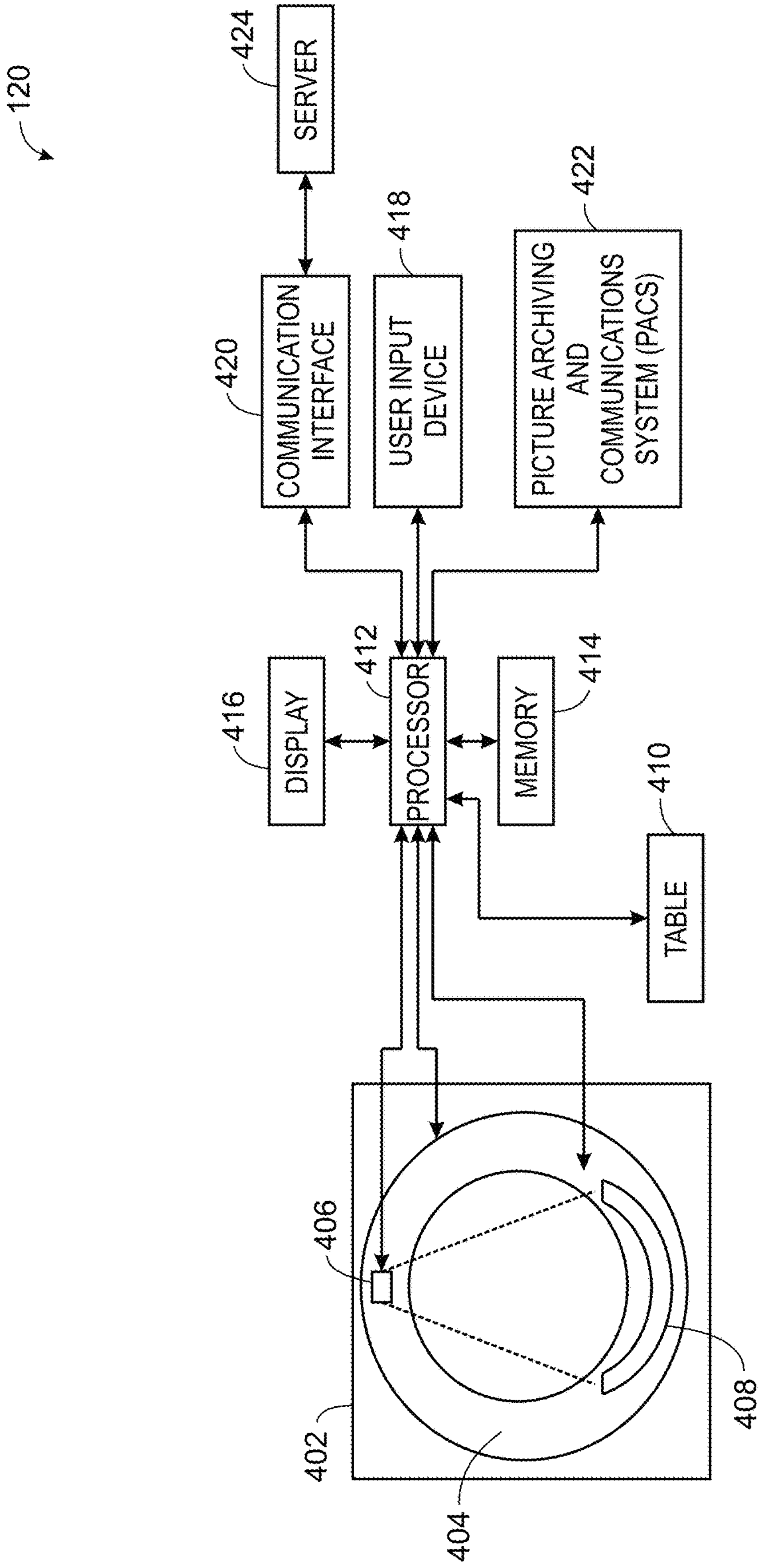
FIG. 4 is a diagram of an example preoperative imaging system of FIG. 1.

FIG. 4 is a diagram of an example preoperative imaging system 120 of FIG. 1. As shown in FIG. 4, the preoperative imaging system 120 may include a gantry 402, a rotational frame 404, an X-ray source 406, an X-ray detector 408, a table 410, a processor 412, a memory 414, a display 416, a user input device 418, a communication interface 420, a picture archiving and communications system (PACS) 422, and a server 424.

The processor 412 may be configured to control operations of the preoperative imaging system 120. For example, the processor 412 may be a CPU, a GPU, an APU, a microprocessor, a microcontroller, a DSP, an FPGA, an ASIC, or the like. The processor 412 may be implemented in hardware, firmware, or a combination of hardware and software. The processor 412 may include one or more processors 412 configured to perform the operations described herein. For example, a single processor 412 may be configured to perform all of the operations described herein. Alternatively, multiple processors 412, collectively, may be configured to perform all of the operations described herein, and each of the multiple processors 412 may be configured to perform a subset of the operations described herein. For example, a first processor 412 may perform a first subset of the operations described herein, a second processor 412 may be configured to perform a second subset of the operations described herein, etc.

The processor 412 may be configured to control the gantry 402, movement of the rotational frame 404, the X-ray source 406, the X-ray detector 408, and movement of the table 410.

The memory 414 may be configured to store information and/or instructions for use by the processor 412. The memory 414 may be a non-transitory computer-readable medium. For example, the memory 414 may be a RAM, a ROM, a flash memory, a magnetic memory, an optical memory, or the like. The memory 414 may be configured to store instructions that, when executed by the processor 412, cause the processor 412 to perform the operations described herein.

The display 416 may be configured to display information. For example, the display 416 may be a monitor, an LED display, a cathode ray tube, a projector display, a touchscreen, tablet computer, mobile phone, VR and/or AR glasses, or the like.

The user input device 418 may be configured to receive a user input, and provide the user input to the processor 412. For example, the user input device 418 may be a touch screen display, a keyboard, a keypad, a mouse, a button, a switch, a microphone, or the like. Additionally, or alternatively, the user input device 418 may be configured to sense information. For example, the user input device 418 may sense information from an electro-magnetic positioning system, an inertial measurement system, an accelerometer, a gyroscope, an actuator, or the like.

The communication interface 420 may be configured to enable the processor 412 to communicate with other devices, such as via a wired connection, a wireless connection, or a combination of wired and wireless connections. For example, the communication interface 420 may include an Ethernet interface, an optical interface, a coaxial interface, an infrared interface, an RF interface, a USB interface, a Wi-Fi interface, a cellular network interface, or the like. The PACS 422 may be configured to communicate with external systems and/or networks to permit users at various locations to access the medical image. The server 424 may be configured to store one or more models as described herein. For example, the server 424 may be an on-premises server, a cloud server, a virtual machine, or the like.

The number and arrangement of the components of the preoperative imaging system 120 shown in FIG. 4 are provided as an example. In practice, the preoperative imaging system 120 may include additional components, fewer components, different components, or differently arranged components than those shown in FIG. 4. Additionally, or alternatively, a set of components (e.g., one or more components) of the preoperative imaging system 120 may perform one or more functions described as being performed by another set of components of the preoperative imaging system 120.

Figure 5:
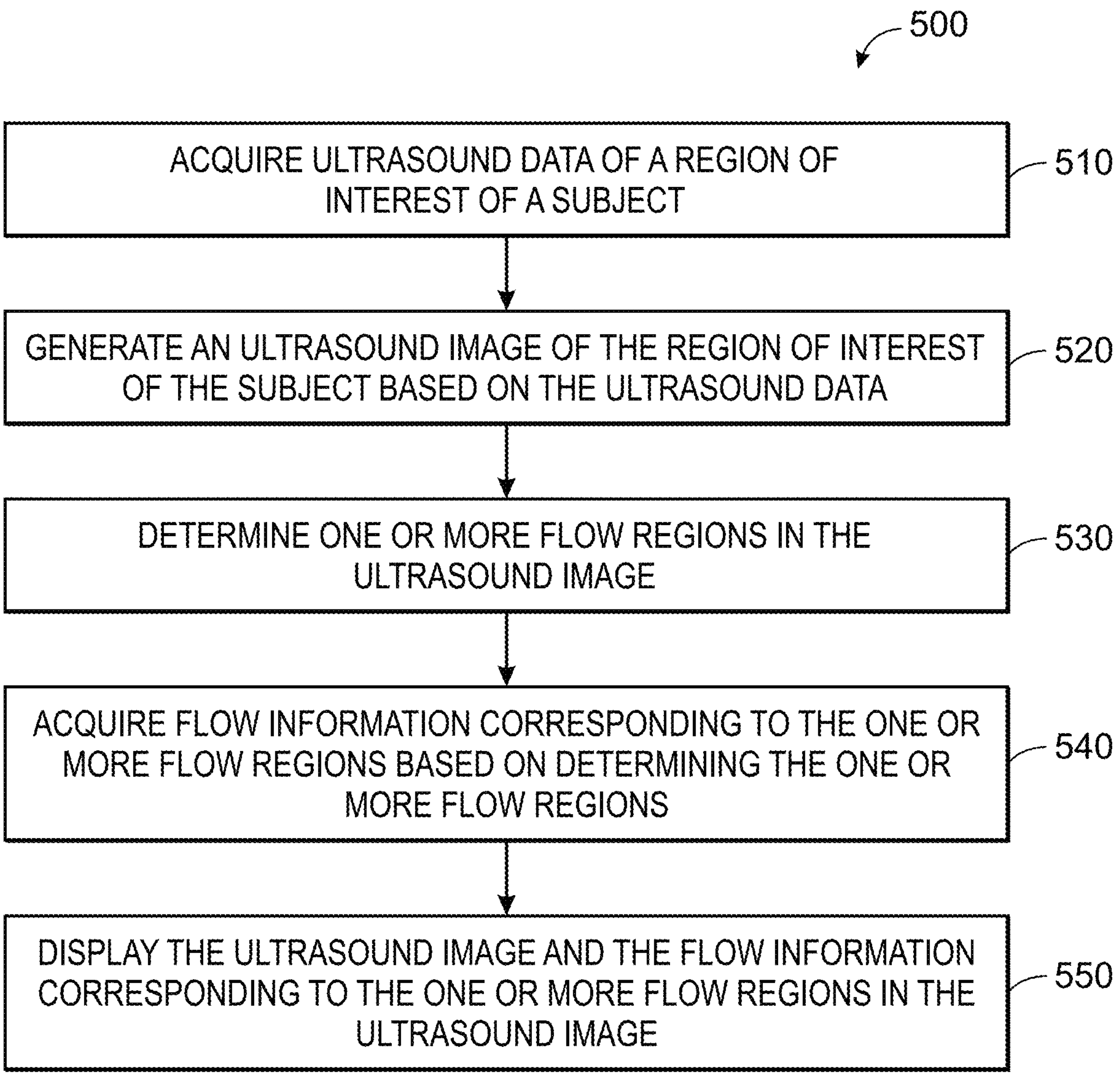
FIG. 5 is a flowchart of an example process for automatically determining flow regions in an ultrasound image and displaying flow information in the flow regions.

FIG. 5 is a flowchart of an example process 500 for automatically determining flow regions in an ultrasound image and displaying flow information in the flow regions.

As shown in FIG. 5, the process 500 may include acquiring ultrasound data of a region of interest of a subject (operation 510). For example, the ultrasound system 110 may acquire ultrasound data of a region of interest of a subject based on a user of the ultrasound system 110 positioning the ultrasound probe 202 relative to the subject. The region of interest of the subject may include one or more regions that exhibit fluid flow.

As further shown in FIG. 5, the process 500 may include generating an ultrasound image of the region of interest of the subject based on the ultrasound data (operation 520). For example, the ultrasound system 110 may generate an ultrasound image of the region of interest of the subject based on the ultrasound data. The ultrasound image may be a B-mode image, or the like.

As further shown in FIG. 5, the process 500 may include determining one or more flow regions in the ultrasound image (operation 530). For example, the ultrasound system 110 may determine one or more flow regions in the ultrasound image. The one or more flow regions may be regions of the ultrasound image that might exhibit fluid flow. Restated, the one or more flow regions may be regions of the ultrasound image that correspond to blood vessels or other structures in which fluid flows.

According to an embodiment, the ultrasound system 110 may determine the one or more flow regions in the ultrasound image using an image processing technique. For example, the image processing technique may be a segmentation technique, a pattern matching technique, a feature extraction technique, an image analysis technique, an edge detection technique, an image registration technique, or the like. In this case, the ultrasound system 110 may analyze the ultrasound image using the image processing technique, and determine the one or flow regions based on the analysis. For example, the ultrasound system 110 may analyze the ultrasound image to identify structures that might exhibit fluid flow.

According to another embodiment, the ultrasound system 110 may determine the one or more flow regions in the ultrasound image using an AI model. For example, the ultrasound system 110 may input the ultrasound image into the AI model, and determine the one or more flow regions based on an output of the AI model. The AI model may be a convolutional neural network (CNN) model, a residual neural network, a random forest model, a decision tree model, an artificial neural network (ANN), a Naïve Bayes model, a decision tree, a recurrent neural network (RNN), a logistic regression model, a support vector machine, or the like. In this case, the AI model may be trained to receive an ultrasound image, analyze the ultrasound image to determine one or more flow regions in the ultrasound image, and output information that identifies the one or more flow regions. The training data may include known ultrasound images that are correlated with known flow regions.

According to an embodiment, the ultrasound system 110 may determine the one or more flow regions in the ultrasound image using preoperative imaging data of the region of interest acquired by the preoperative imaging system 120. For example, the ultrasound system 110 may register the ultrasound image with a preoperative image, of a preoperative imaging dataset, acquired by the preoperative imaging system 120 that identifies the one or more flow regions, and determine the one or more flow regions based on registering the ultrasound image with a preoperative image. In this case, the preoperative imaging data may identify the one or more flow regions. In an embodiment, the preoperative imaging data may be automatically analyzed to determine the one or more flow regions. Alternatively, the preoperative imaging data may be manually labelled with the one or more flow regions.

According to an embodiment, the ultrasound system 110 may determine the one or more flow regions in the ultrasound image based on a user input received via the user input device 212. For example, a user of the ultrasound system 110 may interact with the user input device 212 to select the one or more flow regions for which flow information is to be acquired. The ultrasound system 110 may determine the one or more flow regions based on the selection.

According to an embodiment, the ultrasound system 110 may confirm that there is fluid flow in the determined one or more flow regions in the ultrasound image using flow information acquisitions. For example, the ultrasound system 110 may transmit ultrasound signals to the determined flow regions, and determine whether there is fluid flow in the flow regions based on the echo signals corresponding to the flow regions. The ultrasound signals may be scout signals, or the like.

As further shown in FIG. 5, the process 500 may include acquiring flow information corresponding to the one or more flow regions based on determining the one or more flow regions in the ultrasound image (operation 540). For example, the ultrasound system 110 may acquire the flow information using a flow imaging technique. As examples, the flow imaging technique may be power Doppler imaging, color velocity imaging, vector flow imaging, spectral Doppler imaging, or the like. Restated, the flow imaging technique may be any technique for which flow information is acquired by the ultrasound system 110.

According to an embodiment, the flow information may be information that identifies a direction of fluid flow in a flow region. Additionally, or alternatively, the flow information may be information that identifies a velocity of fluid flow in a flow region. Additionally, or alternatively, the flow information may be information that identifies fluid velocity along a CW line over time. Additionally, or alternatively, the flow information may be information that identifies fluid velocity along a PW line and within a PW gate over time.

As further shown in FIG. 5, the process 500 may include displaying the ultrasound image and the flow information corresponding to the one or more flow regions in the ultrasound image (operation 550). For example, the ultrasound system 110 may display the ultrasound image and the flow information corresponding to the one or more flow regions in the ultrasound image.

According to an embodiment, the ultrasound system 110 may display the ultrasound image and the flow information by adjusting respective image parameters of the one or more flow regions. For example, the ultrasound system 110 may display the flow information by adjusting a color, a shading, a brightness, a hue, or the like, of the respective one or more flow regions based on the directions and/or velocities of fluid flow in the one or more flow regions. Additionally, or alternatively, the ultrasound system 110 may display the flow information in the form of power spectra that identifies fluid velocity along the CW line over time. Additionally, or alternatively, the ultrasound system 110 may display the flow information in the form of power spectra that identifies fluid velocity along the PW line and within the PW gate over time.

In this way, the ultrasound system 110 may automatically determine one or more flow regions in an ultrasound image, acquire flow information for the one or more flow regions, and display an ultrasound image and the flow information. In effect, the ultrasound system 110 may display the ultrasound image that displays flow information in such a manner that implies that the ultrasound system 110 acquired flow information for the entire field-of-view of the ultrasound image. However, in practice, the ultrasound system 110 may have only acquired flow information for a subset of the entire field-of-view that corresponds to the determined one or more flow regions. Restated, the ultrasound system 110 may have only acquired flow information for regions of entire field-of-view of the ultrasound image that are likely to have fluid flow. In this way, the ultrasound system 110 may conserve processor and memory resources by only acquiring flow information for a subset of the entire field-of-view as compared to the entire field-of-view. Notwithstanding, the displayed ultrasound image and flow information may display flow information for all of the regions that exhibit fluid flow.

Although FIG. 5 depicts particular operations and a particular sequence of operations, it should be understood that other embodiments may include different operations and/or a different sequence of operations.

Figure 6A:
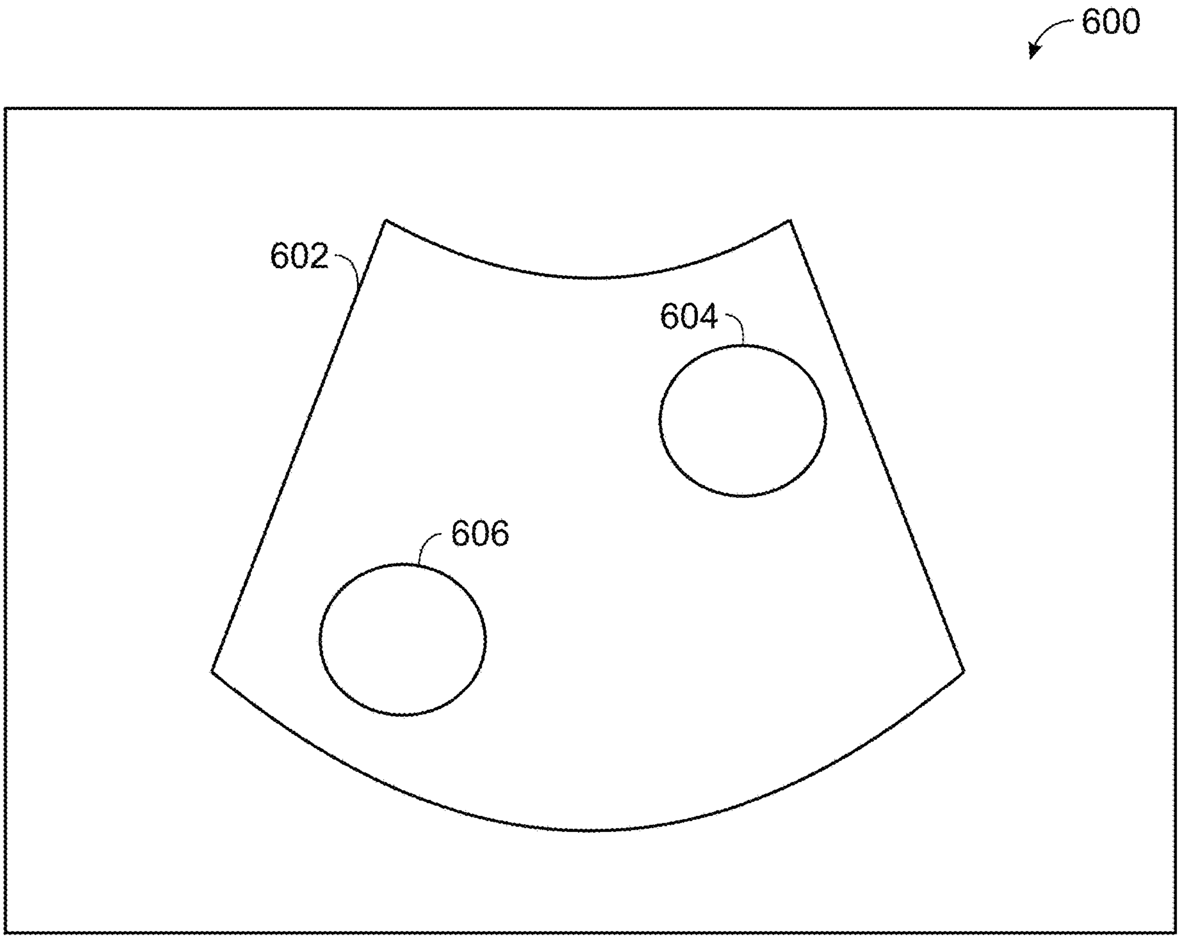
FIGS. 6A and 6B are diagrams of example ultrasound images for displaying flow information in flow regions of the ultrasound image.
Figure 6B:
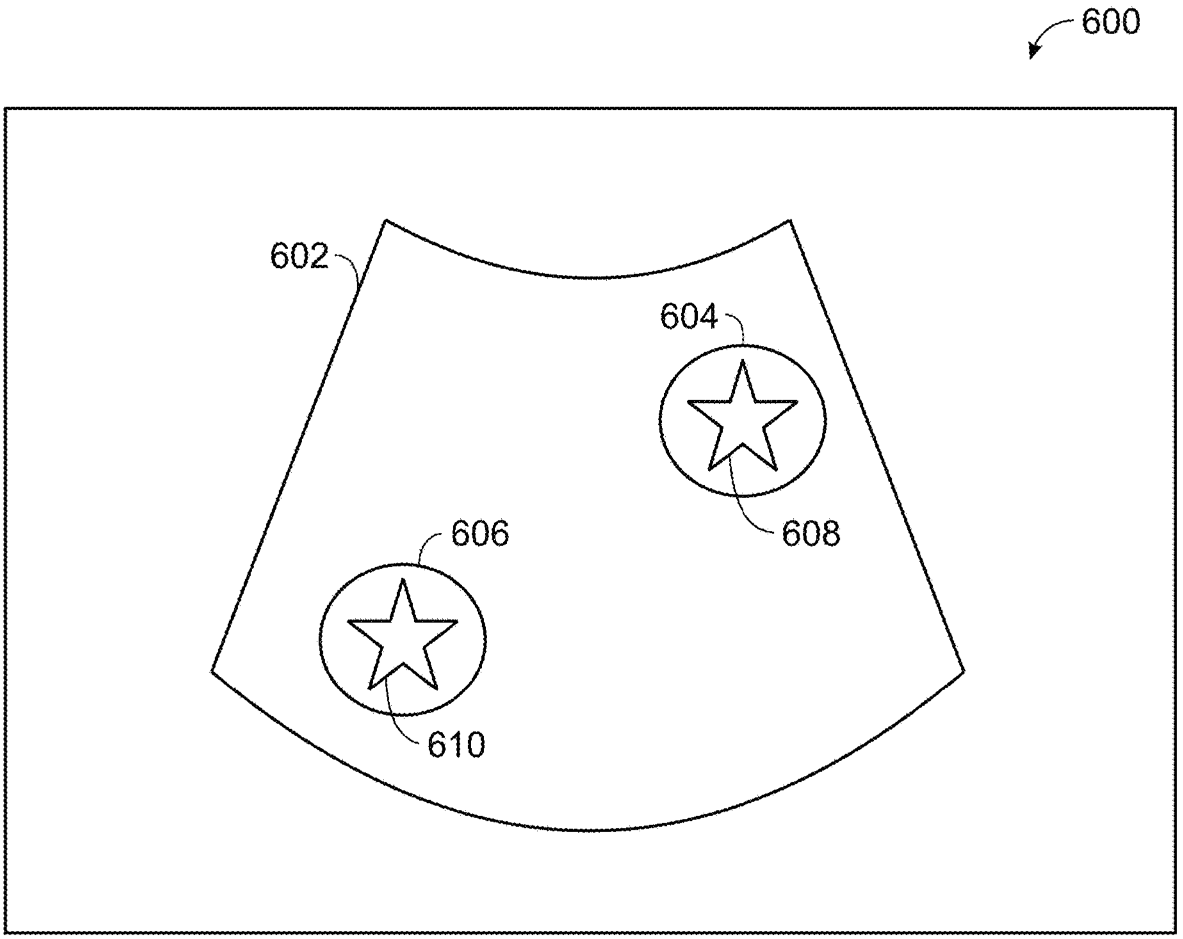

FIGS. 6A and 6B are diagrams 600 of example ultrasound images for displaying flow information in flow regions of the ultrasound image. As shown in FIG. 6A, the ultrasound system 110 may acquire ultrasound data of a region of interest of a subject, and generate an ultrasound image 602 of the region of interest of the subject based on the ultrasound data. As shown, the region of interest may include a first structure 604 that exhibits fluid flow, and may include a second structure 606 that exhibits fluid flow. The ultrasound system 110 may determine one or more flow regions in the ultrasound image 602. For example, the ultrasound system 110 may determine the one or more flow regions in the ultrasound image using a technique described above in connection with operation 530 of FIG. 5. In this case, the ultrasound system 110 may determine a first flow region corresponding to the first structure 604, and may determine a second flow region corresponding to the second structure 606. The ultrasound system 110 may acquire flow information corresponding to the first flow region corresponding to the first structure 604, and may acquire flow information corresponding to the second flow region corresponding to the second structure 606. As shown in FIG. 6B, the ultrasound system 110 may display the ultrasound image 602 including flow information 608 corresponding to the first flow region corresponding to the first structure 604, and including flow information 610 corresponding to the second flow region corresponding to the second structure 606. As shown, although the flow information 608 and the flow information 610 are visually represented using shapes for illustrative purposes, it should be understood that, in practice, the flow information 608 and the flow information 610 may be shown more realistically to denote fluid flow and/or fluid velocity. In this way, the ultrasound system 110 may only acquire flow information for a limited subset of the entire field-of-view of the ultrasound image 602 corresponding to the first flow region and the second flow region. However, in effect, the displayed ultrasound image 602 depicts flow information in such as manner as if the ultrasound system 110 had acquired flow information for the entire field-of-view of the ultrasound image 602. In this way, the embodiments herein provide a more comprehensive ultrasound image that displays more flow information than as compared to conventional techniques that require the selection of a single limited region of the ultrasound image for flow information acquisition, and permit the display of the comprehensive ultrasound image in a manner that conserves processor and/or memory resources of the ultrasound system 110 by virtue of the ultrasound system 110 only acquiring flow information for the regions that are likely to exhibit fluid flow.

Figure 7:
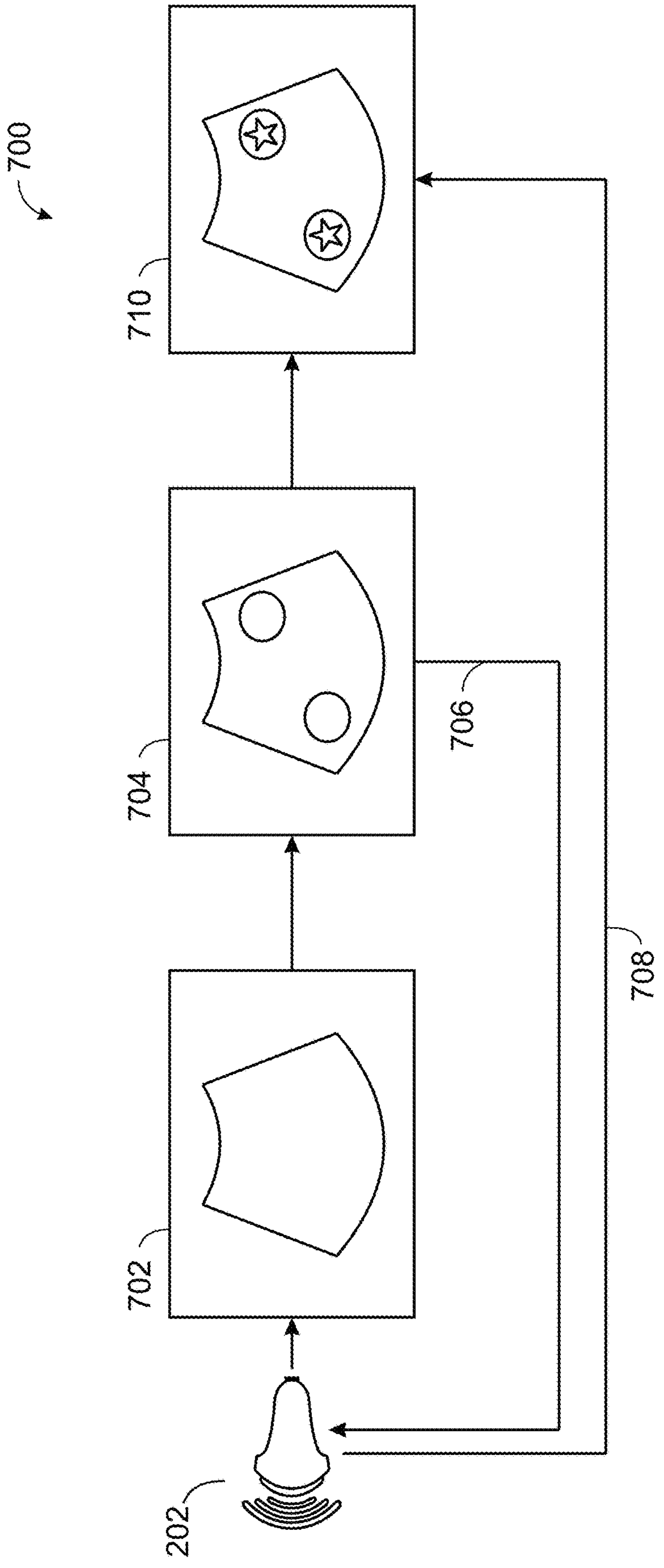
FIG. 7 is a diagram of an example process for automatically determining flow regions in an ultrasound image and displaying flow information in the flow regions.

FIG. 7 is a diagram 700 of an example process for automatically determining flow regions in an ultrasound image and displaying flow information in the flow regions. As shown in FIG. 7, the ultrasound system 110 may acquire, using the ultrasound probe 202, ultrasound data 702 corresponding to a region of interest of a subject. The ultrasound system 110 may generate an ultrasound image 704 of the region of interest of the subject based on the ultrasound data 702. The ultrasound system 110 may determine one or more flow regions in the ultrasound image. For instance, as shown, the ultrasound system 110 may determine a first flow region corresponding to a first structure, and may determine a second flow region corresponding to a second structure. As shown by reference number 706, the ultrasound system 110 may acquire, using the ultrasound probe 202, flow information corresponding to the first flow region and the second flow region based on determining the first flow region and the second flow region. That is, the ultrasound system 110 may control the ultrasound probe 202 to acquire flow information corresponding to the first flow region and the second flow region. The ultrasound system 110 may display the ultrasound image 710 and the flow information corresponding to the first flow region and the second flow region in the ultrasound image 710.

Figure 8:
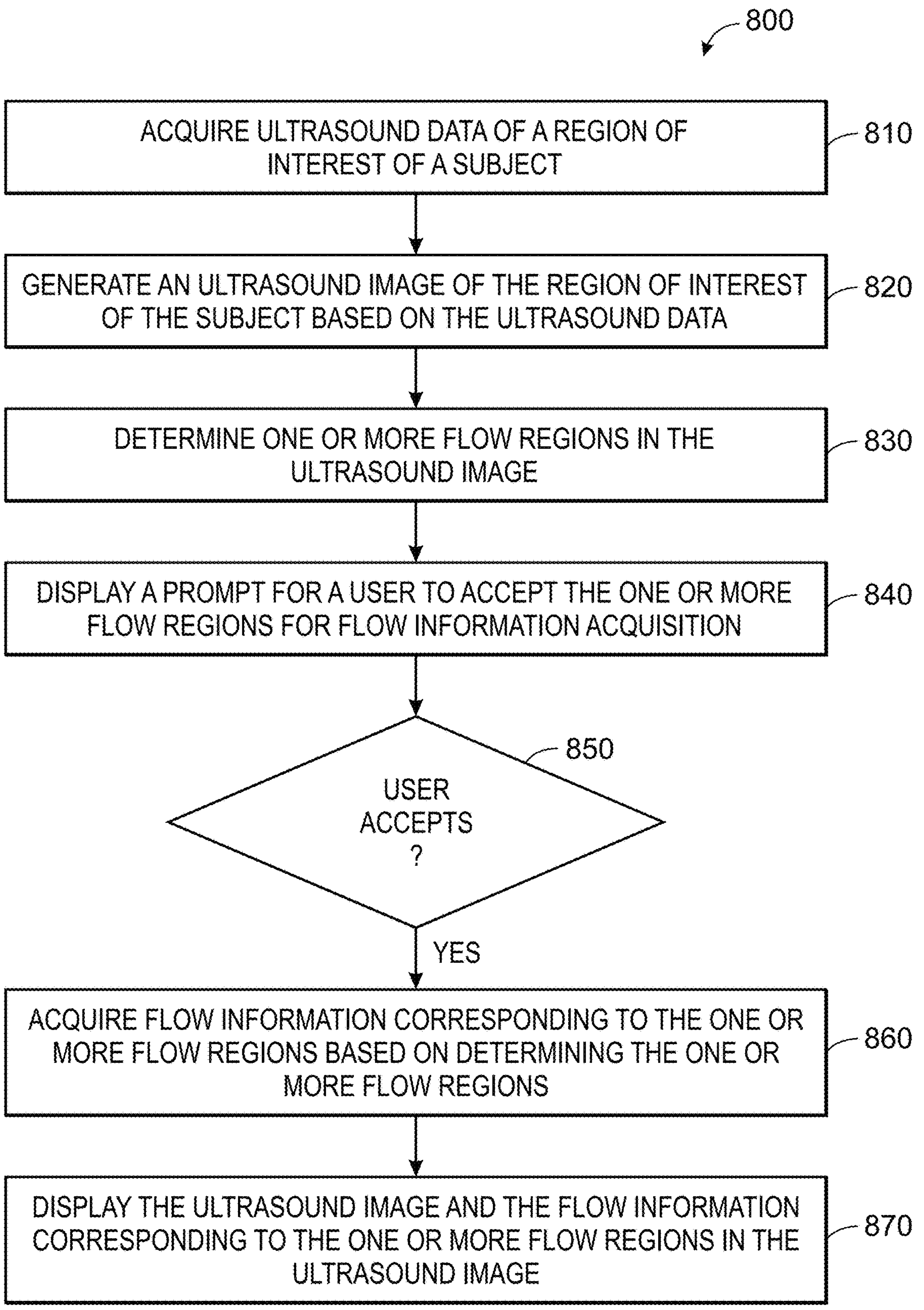
FIG. 8 is a flowchart of an example process for automatically determining flow regions in an ultrasound image and displaying flow information in the flow regions based on a user input.

FIG. 8 is a flowchart of an example process 800 for automatically determining flow regions in an ultrasound image and displaying flow information in the flow regions based on a user input.

As shown in FIG. 8, the process 800 may include acquiring ultrasound data of a region of interest of a subject (operation 810). For example, the ultrasound system 110 may acquire ultrasound data of the region of interest of the subject in a similar manner as described above in connection with operation 510 of FIG. 5.

As further shown in FIG. 8, the process 800 may include generating an ultrasound image of the region of interest of the subject based on the ultrasound data (operation 820). For example, the ultrasound system 110 may generate an ultrasound image of the region of interest of the subject based on the ultrasound data in a similar manner as described above in connection with operation 520 of FIG. 5.

As further shown in FIG. 8, the process 800 may include determining one or more flow regions in the ultrasound image (operation 830). For example, the ultrasound system 110 may determine or more flow regions in the ultrasound image in a similar manner as described above in connection with operation 530 of FIG. 5.

As further shown in FIG. 8, the process 800 may include displaying a prompt for a user to accept the one or more flow regions for flow information acquisition (operation 840). For example, the ultrasound system 110 may display a prompt for the user to accept the one or more flow regions. The prompt may include one or more visual indicators that respectively corresponds to the one or more flow regions. For instance, the visual indicators may delineate the one or more flow regions so that the user can visually assess the determined one or more flow regions as determined by the ultrasound system 110. Additionally, or alternatively, the visual indicators may delineate the one or more flow region for which the flow information is to be acquired. In this way, the user can assess the accuracy of the ultrasound system 110 in determining the one or more flow regions. The prompt may include one or more user interface elements that respectively permit the user to accept, or reject, the one or more determined flow regions. The user can visually assess whether the determined one or more flow regions likely actually include fluid flow, and can interact with the one or more user interface elements to accept, or reject, the determined flow regions based on the assessment.

As further shown in FIG. 8, the process 800 may include determining whether the user accepts the one or more flow regions for flow information acquisition (operation 850). For example, the ultrasound system 110 may determine whether the user accepts the one or more flow regions. The ultrasound system 110 may receive one or more selections that respectively accept, or reject, the one or more determined flow regions. If the ultrasound system 110 determines that the user has rejected a determined flow region, the ultrasound system 110 may refrain from acquiring flow information from the rejected flow region. Alternatively, if the ultrasound system 110 determines that the user has accepted a determined flow region, then the ultrasound system 110 may proceed to operations 860 and 870.

As further shown in FIG. 8, the process 800 may include acquiring flow information corresponding to the one or more flow regions based on determining the one or more flow regions in the ultrasound image (operation 860). For example, the ultrasound system 110 may acquire flow information corresponding to the one or more flow regions based on determining the one or more flow regions in the ultrasound image in a similar manner as described above in connection with operation 540 of FIG. 5.

As further shown in FIG. 8, the process 800 may include displaying the ultrasound image and the flow information corresponding to the one or more flow regions in the ultrasound image (operation 870). For example, the ultrasound system 110 may display the ultrasound image and the flow information corresponding to the one or more flow regions in the ultrasound image in a similar manner as described above in connection with operation 550 of FIG. 5.

Although FIG. 8 depicts particular operations and a particular sequence of operations, it should be understood that other embodiments may include different operations and/or a different sequence of operations.

Figure 9A:
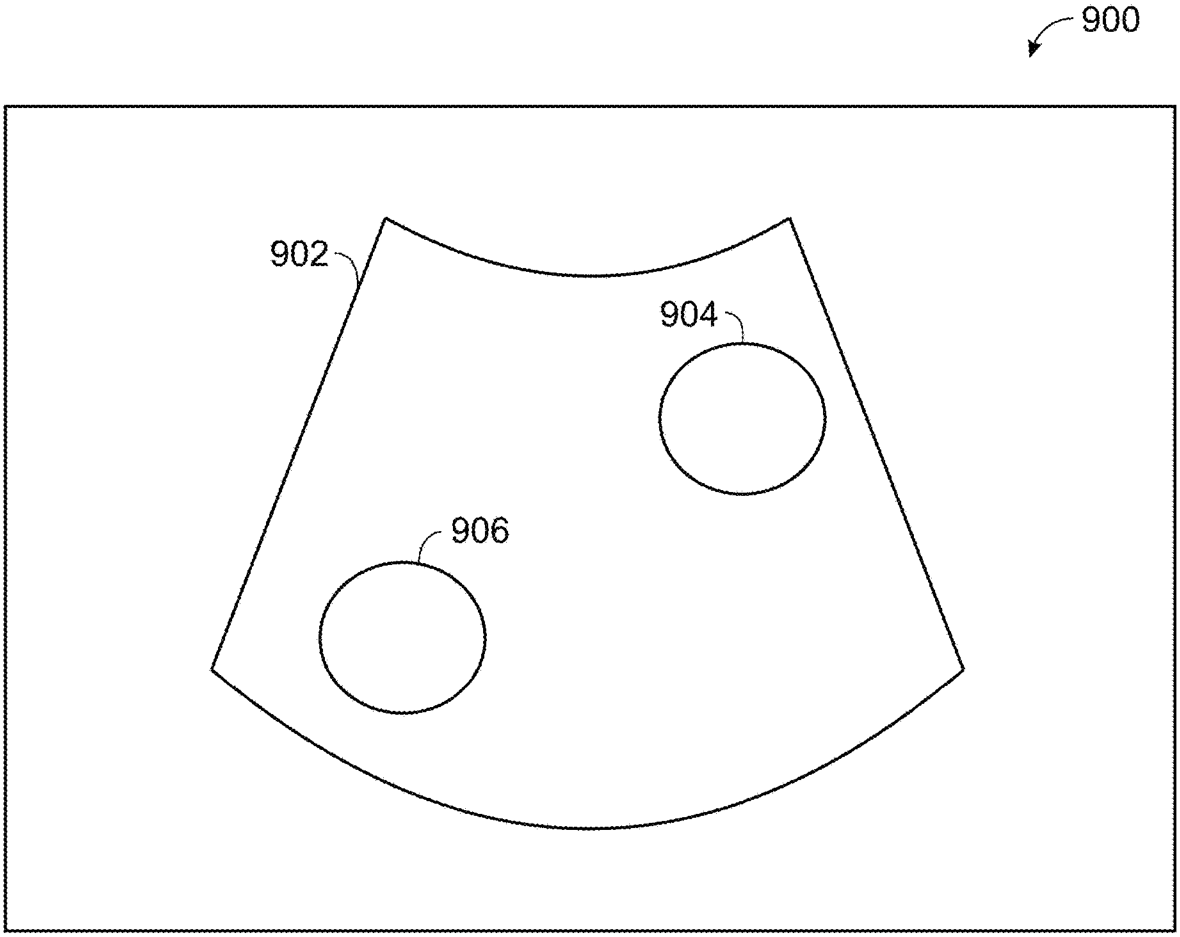
FIGS. 9A and 9B are diagrams of an example process for automatically determining flow regions in an ultrasound image and acquiring flow information for the flow regions.
Figure 9B:
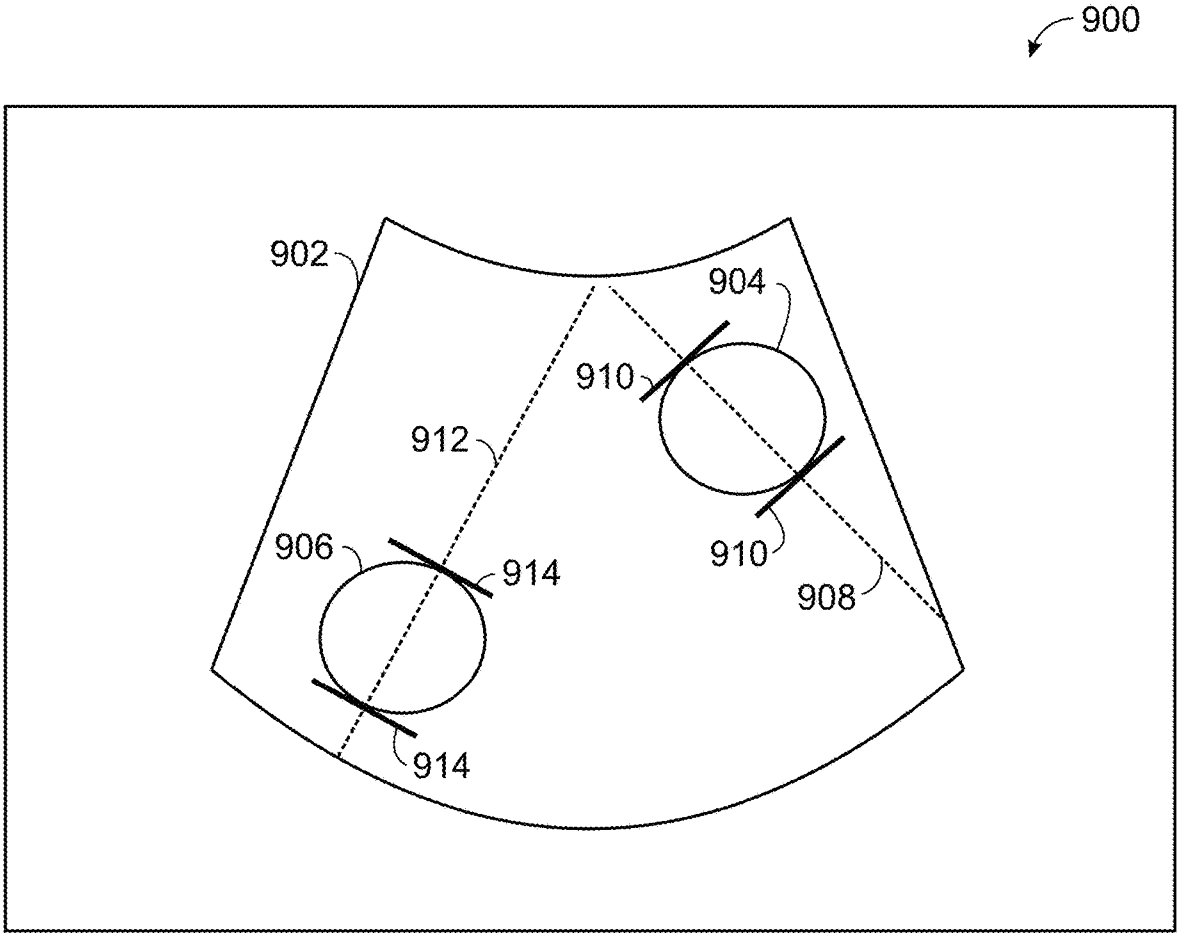

FIGS. 9A and 9B are diagrams 900 of an example process for automatically determining flow regions in an ultrasound image and acquiring flow information for the flow regions. As shown in FIG. 9A, the ultrasound system 110 may acquire ultrasound data of a region of interest of a subject, and generate an ultrasound image 902 of the region of interest of the subject based on the ultrasound data. As shown, the region of interest may include a first structure 904 that exhibits fluid flow, and may include a second structure 906 that exhibits fluid flow. The ultrasound system 110 may determine one or more flow regions in the ultrasound image 902. For example, the ultrasound system 110 may determine the one or more flow regions in the ultrasound image using a technique described above in connection with operation 530 of FIG. 5. In this case, the ultrasound system 110 may determine a first flow region corresponding to the first structure 904, and may determine a second flow region corresponding to the second structure 906. The ultrasound system 110 may position a PW line and a PW gate for each of the determined flow regions. For example, as shown, the ultrasound system 110 may set a first PW line 908 to traverse the first structure 904 and may set a first PW gate 910 to delineate the first structure 904. Further, as shown, the ultrasound system 110 may set a second PW line 912 to traverse the second structure 906 and may set a second PW gate 914 to delineate the second structure 906. The ultrasound system 110 may acquire flow information that identifies fluid velocity along the first PW line 908 and within the first PW gate 910 over time, and may acquire flow information that identifies fluid velocity along the second PW line 912 and within the second PW gate 914 over time. The ultrasound system 110 may display the flow information in the form of power spectra that that identifies fluid velocity along the first PW line 908 and within the first PW gate 910 over time, and may acquire flow information that identifies fluid velocity along the second PW line 912 and within the second PW gate 914 over time.

According to an embodiment, the ultrasound system 110 may use one or more AI models. The one or more AI models may be associated with a training phase, a deployment phase, and a monitoring phase. In the training phase, the ultrasound system 110 may receive and process training data to generate a trained model. The training data may be generated, received, or otherwise obtained from internal and/or external resources.

Generally, the trained model may include a set of variables (e.g., nodes, neurons, filters, or the like) that are tuned (e.g., weighted, biased, or the like) to different values via the application of the training data. According to an embodiment, the training process may employ supervised, unsupervised, semi-supervised, and/or reinforcement learning processes to train the model. According to an embodiment, a portion of the training data may be withheld during training and/or used to validate the trained model.

For supervised learning processes, the training data may include labels or scores that may facilitate the training process by providing a ground truth. For example, the labels or scores may indicate an output of the model. Training may proceed by feeding a training dataset including the training data into the model. The model may have variables set at initialized values (e.g., at random, based on Gaussian noise, based on pre-trained values, or the like). The model may generate an output based on the training dataset being input to the model. The output may be compared with the corresponding label or score (e.g., the ground truth) indicating the known output, which may then be back-propagated through the model to adjust the values of the variables. This process may be repeated for a plurality of samples at least until a determined loss or error is below a predefined threshold. According to an embodiment, some of the training data may be withheld and used to further validate or test the trained model.

For unsupervised learning processes, the training data may not include pre-assigned labels or scores to aid the learning process. Instead, unsupervised learning processes may include clustering, classification, or the like, to identify naturally occurring patterns in the training data. As an example, the training data may be clustered into groups based on identified similarities and/or patterns. K-means clustering or K-Nearest Neighbors may also be used, which may be supervised or unsupervised. Combinations of K-Nearest Neighbors and an unsupervised cluster technique may also be used. For semi-supervised learning, a combination of training data with pre-assigned labels or scores and training data without pre-assigned labels or scores may be used to train the model.

When reinforcement learning is employed, an agent (e.g., an algorithm) may be trained to make a decision from the training data through trial and error. For example, based on making a decision, the agent may then receive feedback (e.g., a positive reward if the prediction was above a predetermined threshold), adjust its next decision to maximize the reward, and repeat until a loss function is optimized.

After being trained, the trained model may be stored and subsequently applied by the ultrasound system 110 during the deployment phase. For example, during the deployment phase, the trained model executed by the ultrasound system 110 may receive input data. During the deployment phase, the trained model may perform one or more operations as described in connection with FIG. 5 and/or FIG. 8.

After being deployed, the trained model may be monitored during the monitoring phase. For example, during the monitoring phase, the model may generate monitoring data that is used to monitor the trained model. The monitoring data may include data that identifies an output as determined by an operator. During the monitoring phase, monitoring data may be analyzed along with the predicted output data and input data to determine an accuracy of the trained model. According to an embodiment, based on the analysis, the process may return to the training phase, where values of one or more variables of the model may be adjusted to improve the accuracy of the model.

In this way, some embodiments herein provide an ultrasound system that automatically determines one or more flow regions in the ultrasound image and displays flow information in the one or more flow regions. Further, in this way, the ultrasound system reduces the need for a manual user input of setting a particular region of the ultrasound image for flow information acquisition, and increases the amount of flow information that is capable of being displayed in real-time on the ultrasound image. Accordingly, some embodiments herein provide an improvement to the technical field of ultrasound imaging, provide an improvement to user interfaces of ultrasound systems, and provide an improvement to ultrasound systems by reducing the amount of user inputs for flow information acquisition and by improving the amount of flow information that is capable of being displayed in real-time on the ultrasound image.

In effect, the ultrasound system may display an ultrasound image that displays flow information in such a manner that implies that the ultrasound system acquired flow information for the entire field-of-view of the ultrasound image. However, in practice, the ultrasound system may have only acquired flow information for a subset of the entire field-of-view that corresponds to the determined one or more flow regions. Restated, the ultrasound system may have only acquired flow information for regions of entire field-of-view of the ultrasound image that are likely to have fluid flow. In this way, the ultrasound system may conserve processor and memory resources by only acquiring flow information for a subset of the entire field-of-view as compared to the entire field-of-view, and may improve frame rate by only acquiring flow information for a subset of the entire field-of-view. Notwithstanding, the displayed ultrasound image and flow information may display flow information for all of the regions that exhibit fluid flow.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound system comprising:

a memory configured to store instructions; and one or more processors configured to execute the instructions to:

acquire ultrasound data of a region of interest of a subject;

generate an ultrasound image of the region of interest of the subject based on the ultrasound data;

determine one or more flow regions in the ultrasound image;

display a prompt to a user of the ultrasound system that prompts the user to accept respective one or more locations of the one or more flow regions;

acquire flow information corresponding to the one or more flow regions based on the user accepting the respective one or more locations of the one or more flow regions; and display the ultrasound image and the flow information corresponding to the one or more flow regions in the ultrasound image.

2. The ultrasound system of claim 1, wherein the one or more processors are configured to determine the one or more flow regions using an image processing technique.

3. The ultrasound system of claim 1, wherein the one or more processors are configured to determine the one or more flow regions using an artificial intelligence model.

4. The ultrasound system of claim 1, wherein the one or more processors are configured to determine the one or more flow regions using preoperative imaging data of the region of interest of the subject acquired by a preoperative imaging system.

5. The ultrasound system of claim 1, wherein the one or more processors are configured to automatically acquire the flow information corresponding to the one or more flow regions without receiving a user input that sets respective one or more locations of the one or more flow regions.

6. The ultrasound system of claim 1, wherein the one or more processors are configured to refrain from acquiring other flow information corresponding to external regions that are external to the one or more flow regions.

7. The ultrasound system of claim 1, wherein the one or more processors are configured to:

position a Doppler line and a Doppler gate for each of the one or more flow regions.

8. The ultrasound system of claim 1, wherein the one or more processors are configured to acquire flow information only for a subset of an entire field-of-view of the ultrasound image.

9. The ultrasound system of claim 1, wherein the one or more processors are configured to:

transmit ultrasound signals to the one or more flow regions;

confirm fluid flow in the one or more flow regions based on echo signals corresponding to the one or more flow regions; and acquire the flow information corresponding to the one or more flow regions based on confirming the fluid flow.

10. The ultrasound system of claim 9, wherein the ultrasound signals are scout signals.

11. A method comprising:

acquiring ultrasound data of a region of interest of a subject;

generating an ultrasound image of the region of interest of the subject based on the ultrasound data;

determining one or more flow regions in the ultrasound image;

displaying a prompt to a user that prompts the user to accept respective one or more locations of the one or more flow regions;

acquiring flow information corresponding to the one or more flow regions based on d the user accepting the respective one or more locations of the one or more flow regions; and displaying the ultrasound image and the flow information corresponding to the one or more flow regions in the ultrasound image.

12. The method of claim 11, wherein the determining the one or more flow regions comprises determining the one or more flow regions using an image processing technique.

13. The method of claim 11, wherein the determining the one or more flow regions comprises determining the one or more flow regions using an artificial intelligence model.

14. The method of claim 11, wherein the determining the one or more flow regions comprises determining the one or more flow regions using preoperative imaging data of the region of interest of the subject acquired by a preoperative imaging system.

15. The method of claim 11, further comprising:

displaying a prompt to a user of an ultrasound system that prompts the user to accept respective one or more locations of the one or more flow regions.

16. The method of claim 11, wherein the acquiring the flow information comprises acquiring the flow information corresponding to the one or more flow regions without receiving a user input that sets respective one or more locations of the one or more flow regions.

17. A non-transitory computer-readable medium storing instructions that, when executed by one or more processors, cause the one or more processors to:

acquire ultrasound data of a region of interest of a subject;

generate an ultrasound image of the region of interest of the subject based on the ultrasound data;

determine one or more flow regions in the ultrasound image;

display a prompt to a user that prompts the user to accept respective one or more locations of the one or more flow regions;

acquire flow information corresponding to the one or more flow regions based on the user accepting the respective one or more locations of the one or more flow regions; and display the ultrasound image and the flow information corresponding to the one or more flow regions in the ultrasound image.

18. The non-transitory computer-readable medium of claim 17, wherein the instructions further cause the one or more processors to determine the one or more flow regions using an image processing technique.

19. The non-transitory computer-readable medium of claim 17, wherein the instructions further cause the one or more processors to determine the one or more flow regions using an artificial intelligence model.

20. The non-transitory computer-readable medium of claim 17, wherein the instructions further cause the one or more processors to determine the one or more flow regions using preoperative imaging data of the region of interest of the subject acquired by a preoperative imaging system.

* * * * *